US012599494B2

(12) United States Patent　　(10) Patent No.:　US 12,599,494 B2

Positano et al.　　(45) Date of Patent:　Apr. 14, 2026

(54) FORCE REDISTRIBUTION HINDFOOT SHOE INSERT

(71) Applicant: ROXILLA LLC, New York, NY (US)

(72) Inventors: Rock G. Positano, New York, NY (US); Danielle Evin Gerber, New York, NY (US); Robert White, Bloomingdale, NJ (US); Rock CJay Positano, New York, NY (US)

(73) Assignee: ROXILLA LLC, New York, NY (US)

( * ) Notice: Subject to any disclaimer, the term of this patent is extended or adjusted under 35 U.S.C. 154(b) by 295 days.

(21) Appl. No.: 18/296,086

(22) Filed: Apr. 5, 2023

(65) Prior Publication Data

US 2023/0233355 A1　　Jul. 27, 2023

Related U.S. Application Data

(63) Continuation of application No. PCT/US2022/074763, filed on Aug. 10, 2022.

(60) Provisional application No. 63/231,666, filed on Aug. 10, 2021.

(51) Int. Cl.
*A61F 5/14*　　(2022.01)

(52) U.S. Cl.
CPC ..................................... *A61F 5/14* (2013.01)

(58) Field of Classification Search
CPC ........ A61F 5/14; A61F 13/063; A61F 13/064;
A43B 17/006; A43B 17/02; A43B 17/14;
A43B 7/14; A43B 7/142; A43B 7/143;
A43B 7/1445; A43B 21/26; A43B 21/32
See application file for complete search history.

(56) References Cited

U.S. PATENT DOCUMENTS

| | | | |
|---|---|---|---|
| 4,718,179 A | 1/1988 | Brown | |
| 5,138,774 A | 8/1992 | Sarkozi | |
| 2010/0269371 A1 | 10/2010 | Gray | |
| 2016/0219970 A1 | 8/2016 | Jacob | |
| 2017/0164688 A1 | 6/2017 | Weiss | |
| 2017/0280816 A1 | 10/2017 | Lyden | |
| 2018/0192739 A1* | 7/2018 | Granger | ................ A43B 17/14 |

* cited by examiner

*Primary Examiner* — Ophelia A Hawthorne

(74) *Attorney, Agent, or Firm* — Heslin Rothenberg Farley & Mesiti P.C.

(57)　　　　　ABSTRACT

Shoe insert devices that absorb shock and that redistribute forces within a user's foot and/or knee during use. The shoe insert devices include a hindfoot insert portion configured to be positioned within a shoe and extend beneath a hindfoot portion of a sole of a foot of the user with a top side of the hindfoot insert portion facing the sole. The hindfoot insert portion is resilient at least in a thickness direction extending between the top and bottom sides thereof. The hindfoot insert portion includes a fascia projection extending upwardly from the top surface positioned medially between medial and lateral sides of the hindfoot insert portion and being spaced distally from the proximal end, and a lateral projection extending at least one of upwardly from the top surface and downwardly from the bottom surface positioned proximate to the lateral side and distal to the fascia projection.

22 Claims, 16 Drawing Sheets

FORCE REDISTRIBUTION HINDFOOT SHOE INSERT

CROSS-REFERENCE TO RELATED APPLICATION

This application is a by-pass continuation of PCT International Application No. PCT/US2022/074763, filed on Aug. 10, 2022, and entitled Force Redistribution Hindfoot Shoe Insert, which claims priority benefit under 35 U.S.C. § 119(e) of U.S. Provisional Patent Application No. 63/231, 666, filed on Aug. 10, 2021, and entitled Force Redistribution Hindfoot Shoe Insert, which are incorporated herein by reference in their entireties.

FIELD OF THE DISCLOSURE

The present disclosure relates generally to shoe inserts that absorbs shocks and redistributes forces within a user's foot and/or knee during use, and related methods. More specifically, the present disclosure relates to a hindfoot shoe insert that includes a proximal projection and a lateral projection that reducing the tension at the attachment of the plantar fascia into the medial tubercle as well as decrease the loading in the medial part of the knee, and related methods.

BACKGROUND

There are a large variety of shoe inserts available on the market to increase the comfort of the wearer by proving cushioning, shock absorption, and the like. The shoe inserts are configured to lie beneath the sole or bottom of a foot of a user and above the bottom of a shoe (i.e., within a shoe beneath the user's foot). The main thrust in the use of such inserts is to provide a sufficiently thick layer of padding material to cushion any impact. These inserts are typically made of a resilient material, such as cellular polymeric foams, illustratively polyurethanes, heat-sensitive viscoelastic memory foams, or gels and are generally configured to overlie the entire foot bed of the shoe.

Typical inserts are formed as full sole and ball of foot-type inserts. These shoe inserts overlie the area of the foot bed that would be contacted by the ball of the foot and at least a portion of the toes. Ball of foot inserts are particularly useful in conjunction with high heeled shoes to prevent the foot from sliding forward and/or to provide cushioning against the increased forces on the ball of the foot that result from the elevation of the heel.

However, current shoe inserts do not consider plantar fascia considerations, such as treatment of a strained or injured plantar fascia and/or the prevention of such strain or injury to a user's plantar fascia. Still further, current shoe inserts fail to adequately treat knee stress and/or prevent knee stress and development of osteoarthritis therein.

Plantar fasciitis is one of the most common ailments of the foot. It has been estimated that plantar fasciitis affects one in ten people at some stage of their lives. The plantar fascia is a broad band of connective tissue (the largest ligament in the human body) which spans from the heel into the forefoot. Specifically, the plantar fascia is a thick fibrous tissue that extends from the medial tubercle of the calcaneus to the transverse ligaments of the metatarsal heads in the foot. It acts to support the medial longitudinal arch of the foot, and also acts as a dynamic shock absorber. Normally this tissue can withstand very high loads, however it can become irritated either acutely or chronically (e.g., overused or overstretched), and inflammation and pain can result— known as plantar fasciitis. Plantar fasciitis may arise following one or more tears that cause inflammation and symptoms of pain, and has been described as either inflammatory or degenerative (e.g., similar to a tendonosis). Inflammatory changes at the insertion of the plantar fascia into the plantar calcaneal tuberosity can be caused by macro or micro trauma, degenerative changes, or as a local manifestation of a systemic inflammatory process; i.e., rheumatoid arthritis, gout or seronegative spondyloarthropathy, for example.

There are several factors that are associated with plantar fasciitis and are thought to be involved in causing the condition, such as: long periods of time standing up; high-impact sports activities; footwear with poor arch support or cushioning; and overstretching of the sole of the foot. There is a high incidence of plantar fasciitis in athletes, particularly runners, due to the level of stress placed on the feet during such activities. However, plantar fasciitis can occur from a variety of different activities and/or conditions. For example, is thought that several small injuries that occur to the plantar fascia often accumulate and cause the gradual onset of the condition.

There is, therefore, a need for improved shoe inserts that address the deficiencies of current shoe inserts.

SUMMARY

Hindfoot shoe inserts (and methods utilizing such inserts) that absorb shock and that redistribute forces within a user's foot and/or knee during use are disclosed herein. The hindfoot shoe inserts and related methods of the present disclosure include projections that are configured to reduce the tension at the attachment of the plantar fascia and the medial tubercle of the calcaneus bone of a user. The hindfoot shoe inserts and related methods of the present disclosure are also configured to decrease the loading in the medial part of the knee of a user. The hindfoot shoe inserts and related methods of the present disclosure are also configured to reduce the amount of stress in the heel fat pad of a user. The hindfoot shoe inserts and related methods of the present disclosure may further be configured to reduce the stress on the lateral ankle ligaments, lower back, pelvis/pelvic posture, and/or Achilles tendon of a user.

In one aspect, the present disclosure provides a shoe insert device comprising a hindfoot insert portion comprising a proximal end, a distal end, a medial side extending between the proximal and distal ends, a lateral side extending between the proximal and distal ends, a top side, and a bottom side. The hindfoot insert portion is configured to be positioned within a shoe and extend beneath a hindfoot portion of a sole of a foot of a user within the shoe with the top side of the hindfoot insert portion facing the sole. The hindfoot insert portion is resilient at least in a thickness direction extending between the top and bottom sides. The hindfoot insert portion comprises: a fascia projection extending upwardly from the top surface positioned medially between the medial and lateral sides and being spaced distally from the proximal end; and a lateral projection extending at least one of upwardly from the top surface and downwardly from the bottom surface positioned proximate to the lateral side and distal to the fascia projection.

In some embodiments, the fascia projection is extended along the medial-lateral direction such that it defines a length along the medial-lateral direction that is greater than its length along the proximal-distal direction. In some embodiments, the fascia projection defines a length along the medial-lateral direction of at least about 2 cm. In some embodiments, the fascia projection defines a length along the medial-lateral direction within the range of about 2 cm to about 5 cm.

In some embodiments, the fascia projection defines a length along the proximal-distal direction of less than about 1½ cm. In some embodiments, the fascia projection defines a length along the proximal-distal direction within the range of about ½ cm to about 1½ cm.

In some embodiments, the fascia projection defines a maximum height from the top surface adjacent to the fascia projection of at least about ¼ inch. In some embodiments, the fascia projection defines a maximum height from the top surface adjacent to the fascia projection within the range of about ¼ inch to about ¾ inch.

In some embodiments, fascia projection is spaced distally from the proximal end within the range of about 1 inch to about 3 inches. In some embodiments, the fascia projection is spaced distally from the proximal end within the range of about 1½ inches to about 2¾ inches.

In some embodiments, the fascia projection is resilient at least along the thickness direction. In some embodiments, the fascia projection is convex along the proximal-distal direction. In some embodiments, the fascia projection is arcuately convex along the proximal-distal direction. In some embodiments, the fascia projection includes a cylindrical-shaped portion that extends along the medial-lateral direction.

In some embodiments, a proximal portion of the lateral projection is aligned with at least a portion of the fascia projection along the proximal-distal direction. In some other embodiments, the lateral projection is spaced from the fascia projection along the proximal-distal direction.

In some embodiments, the lateral projection is convex along the proximal-distal direction. In some embodiments, the lateral projection is arcuately convex along the proximal-distal direction. In some embodiments, the lateral projection is convex along the medial-lateral direction. In some embodiments, the lateral projection includes a lateral portion that is positioned further away from the top surface than a medial portion thereof. In some embodiments, the lateral projection extends downwardly from a lateral side thereof to a medial side thereof. In some embodiments, the lateral projection extends arcuately downwardly from a lateral side thereof to a medial side thereof.

In some embodiments, the lateral projection defines a length along the medial-lateral direction of less than about 1½ inches. In some embodiments, the lateral projection defines a length along the medial-lateral direction within the range of about ½ inch to about 1½. In some embodiments, the lateral projection defines a length along the proximal-distal direction of less than about 2½ inches. In some embodiments, the lateral projection defines a length along the proximal-distal direction within the range of about ½ inch to about 2 inches.

In some embodiments, the lateral projection extends upwardly from the top surface. In some embodiments, the lateral projection defines a maximum height from the top surface adjacent to the lateral projection of at least about ¼ inch. In some embodiments, the lateral projection defines a maximum height from the top surface adjacent to the lateral projection within the range of about ¼ inch to about ¾ inch. In some embodiments, the lateral projection defines a first maximum height from the top surface adjacent to the lateral projection, and the fascia projection defines a second maximum height from the top surface adjacent to the fascia projection, and wherein the first maximum height is within 25% of the second maximum height. In some embodiments, the lateral projection defines a first maximum height from the top surface adjacent to the lateral projection, and the fascia projection defines a second maximum height from the top surface adjacent to the fascia projection, and wherein the first maximum height is less than the second maximum height.

In some embodiments, the hindfoot insert portion includes a proximal portion that is configured to extend beneath a heal fat pad of a heal of the foot of the user that defines the proximal end and a proximal portion of the top surface, and a distal portion that extends distally from the proximal portion and defines the distal end and a distal portion of the top surface, and wherein the a thickness of the distal portion varies such that the distal portion of the top surface extends downward from the proximal portion of the top surface. In some such embodiments, the proximal portion of the top surface is substantially planar. In some such embodiments, the distal portion of the top surface is substantially planar. In some such embodiments, the fascia projection is positioned on the proximal portion of the hindfoot insert portion. In some such embodiments, at least a portion of the lateral projection is positioned on the distal portion of the hindfoot insert portion. In some such embodiments, the at least a portion of the lateral projection is positioned on the proximal portion of the hindfoot insert portion.

In some embodiments, the lateral projection is resilient at least along the thickness direction. In some such embodiments, the fascia projection and the lateral projection have substantially the same modulus of resilience at least along the thickness direction. In some such embodiments, the fascia projection and the lateral projection are formed of the same material. In some embodiments, the lateral projection extends downward from the bottom surface. In some such embodiments, the lateral projection defines a maximum height from the bottom surface adjacent to the lateral projection of at least about ¼ inch. In some such embodiments, the lateral projection defines a maximum height from the bottom surface adjacent to the lateral projection within the range of about ¼ inch to about ¾ inch. In some such embodiments, the lateral projection extends upwardly from the top surface and downwardly from the bottom surface, wherein the lateral projection defines a first maximum height from the bottom surface adjacent to the lateral projection and a second maximum height from the top surface adjacent to the lateral projection, and wherein the first maximum height is within 25% of the second maximum height. In some such embodiments, the first maximum height and the second maximum height are equal. In some such embodiments, the lateral projection comprises a first portion that extends upwardly from the top surface that includes a first modulus of resilience, a second portion that extends downwardly from the bottom surface that includes a second modulus of resilience that differ from the first modulus of resilience. In some such embodiments, the first modulus of resilience is greater than the second modulus of resilience.

The shoe insert device according to any one of the preceding claims, wherein the hindfoot insert portion further comprises a peripheral rim member that extends upwardly from the top surface and along the medial side, proximal end, and lateral side. In some such embodiments, the rim member extends along only a portion of the medial and lateral sides. In some such embodiments, the rim member is arcuately concave as it extends from the top surface. In some such embodiments, the lateral projection extends medially from the rim member. In some such embodiments, the bottom surface is substantially planar.

In some embodiments, the device consists of the hindfoot insert portion. In some embodiments, the proximal end of the hindfoot insert portion defines a proximal free end of the device, the distal end of the hindfoot insert portion defines a distal free end of the device, the medial side of the hindfoot insert portion defines a medial free end of the device, and the lateral side of the hindfoot insert portion defines a lateral free end of the device.

In some embodiments, the device further comprises a base portion configured to couple with the hindfoot insert portion. In some such embodiments, the bottom surface of the hindfoot insert portion includes at least one engagement peg extending away therefrom configured to engage within at least one corresponding engagement cavity in a top side of the base portion.

In some such embodiments, the base portion includes a forefoot portion that is configured to be positioned within the shoe and extend beneath a forefoot portion of the sole of the foot of the user within the shoe. In some such embodiments, the forefoot portion includes a forefoot projection extending upwardly from a top surface thereof. In some such embodiments, the forefoot projection is positioned proximate to a lateral side and distal end of the forefoot portion, and configured to be positioned below a distal, middle and/or proximal phalange of the fourth and/or fifth toes of the foot of the user. In some such embodiments, the base portion includes a midfoot portion that is configured to be positioned within the shoe and extend beneath a midfoot portion of the sole of the foot of the user within the shoe.

In some embodiments, the hindfoot insert portion is an integral portion. In some embodiments, the hindfoot insert portion is of one-piece construction. In some embodiments, the hindfoot insert portion is of multi-piece construction. In some embodiments, at least one of the facia projection and the lateral projection are modular components.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

In another aspect, the present disclosure provides a method of configuring the foot support of a shoe comprising providing hindfoot shoe insert device comprising a proximal end, a distal end, a medial side extending between the proximal and distal ends, a lateral side extending between the proximal and distal ends, a top side and a bottom side. The hindfoot shoe insert device is configured to be positioned within a shoe and extend beneath at least a hindfoot portion of a sole of a foot of a user within the shoe with the top side of the hindfoot shoe insert device facing the sole. The hindfoot shoe insert device is resilient at least in a thickness direction extending between the top and bottom sides. The hindfoot shoe insert device comprises a hindfoot portion comprising: a fascia projection extending upwardly from the top surface positioned medially between the medial and lateral sides and being spaced distally from the proximal end; and a lateral projection extending at least one of upwardly from the top surface and downwardly from the bottom surface positioned proximate to the lateral side and distal to the fascia projection.

In another aspect, the present disclosure provides a method of adjusting a shoe's foot support profile comprising positioning a hindfoot shoe insert device within a hindfoot area of a shoe such that the hindfoot shoe insert device is positioned beneath at least a hindfoot portion of a sole of a foot of a user within the shoe with a top side of the hindfoot shoe insert device facing the sole. The hindfoot shoe insert device comprises a proximal end, a distal end, a medial side extending between the proximal and distal ends, a lateral side extending between the proximal and distal ends, a bottom side and the top side. The hindfoot shoe insert device is resilient at least in a thickness direction extending between the top and bottom sides. The hindfoot shoe insert device comprises a hindfoot portion comprising: a fascia projection extending upwardly from the top surface positioned medially between the medial and lateral sides and being spaced distally from the proximal end; and a lateral projection extending at least one of upwardly from the top surface and downwardly from the bottom surface positioned proximate to the lateral side and distal to the fascia projection.

These and other objects, features and advantages of this disclosure will become apparent from the following detailed description of the various aspects of the disclosure taken in conjunction with the accompanying drawings.

BRIEF DESCRIPTION OF THE DRAWINGS

These and other features, aspects, and advantages of the present disclosure will become better understood when the following detailed description is read with reference to the accompanying drawings. It should be understood that at least some of the drawings are not necessarily to scale (but at least some of the drawings may be drawn to scale). In certain figures, details that are not necessary for an understanding of the disclosure or that render other details difficult to perceive may have been omitted. It should be understood, of course, that the disclosure is not necessarily limited to the particular embodiments illustrated in the figures. Like reference numerals are utilized throughout the figures to represent like aspects illustrated in the drawings, wherein.

DETAILED DESCRIPTION OF THE DRAWINGS

Figure 1:
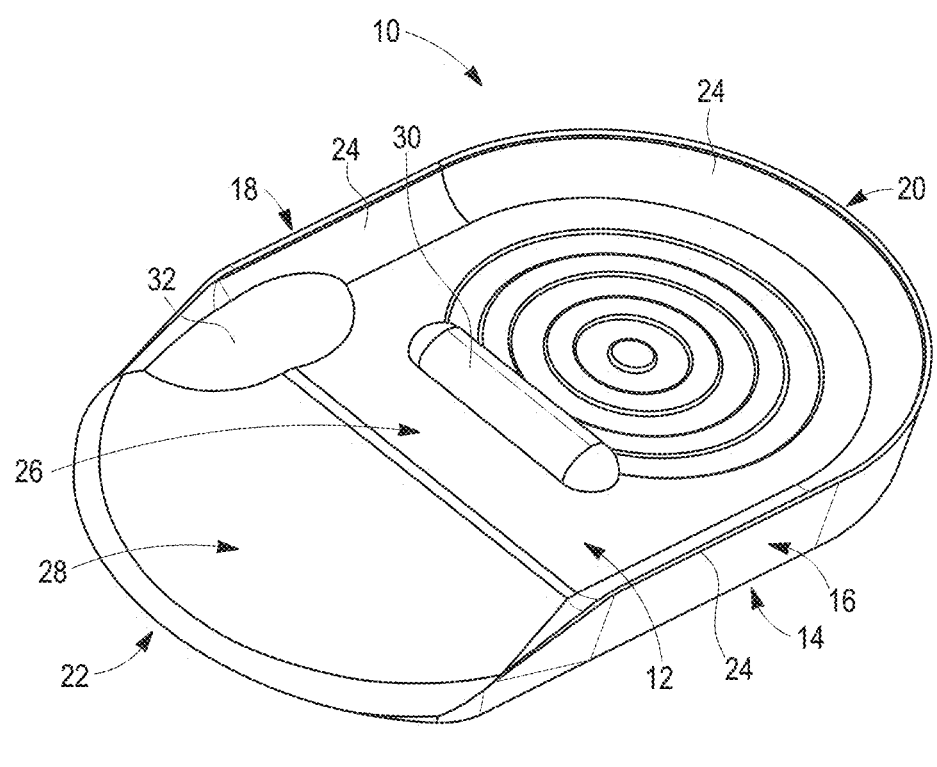
FIG. 1 illustrates an elevational perspective view of a shoe insert device according to an embodiment of the present disclosure.
Figure 2:
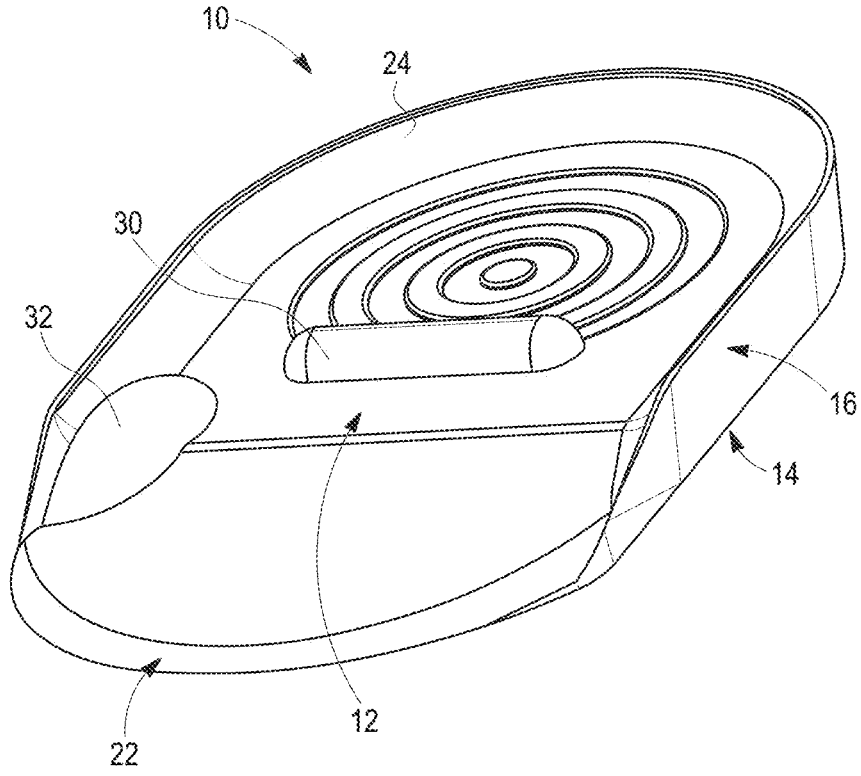
FIG. 2 illustrates another elevational perspective view of the shoe insert device of FIG. 1 according to an embodiment of the present disclosure.
Figure 3:
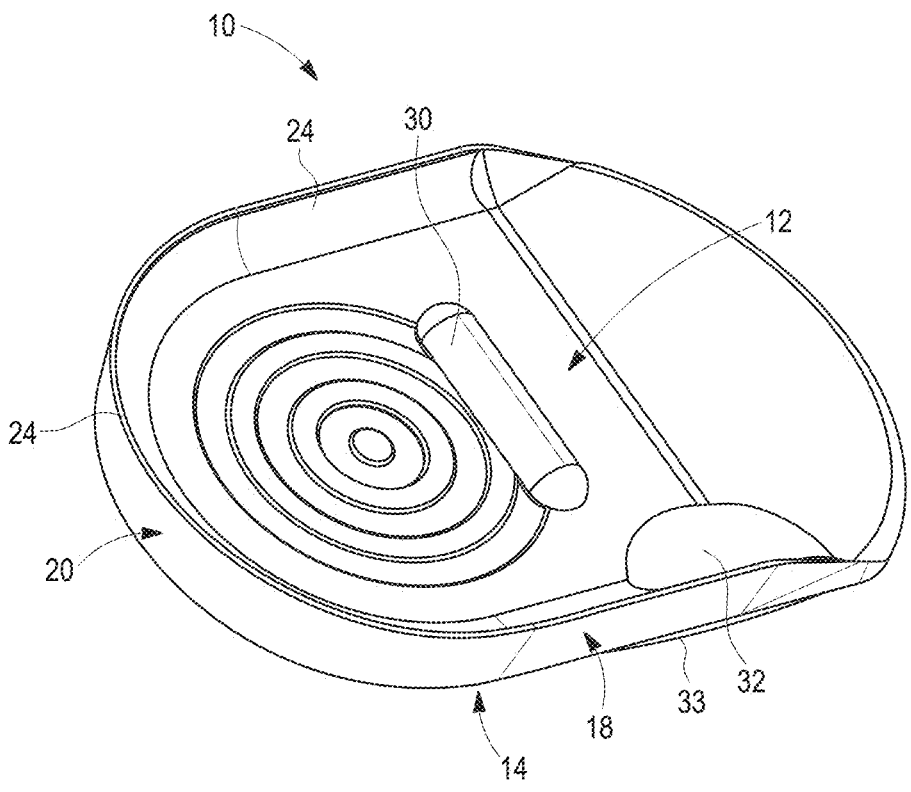
FIG. 3 illustrates another elevational perspective view of the shoe insert device of FIG. 1 according to an embodiment of the present disclosure.
Figure 4:
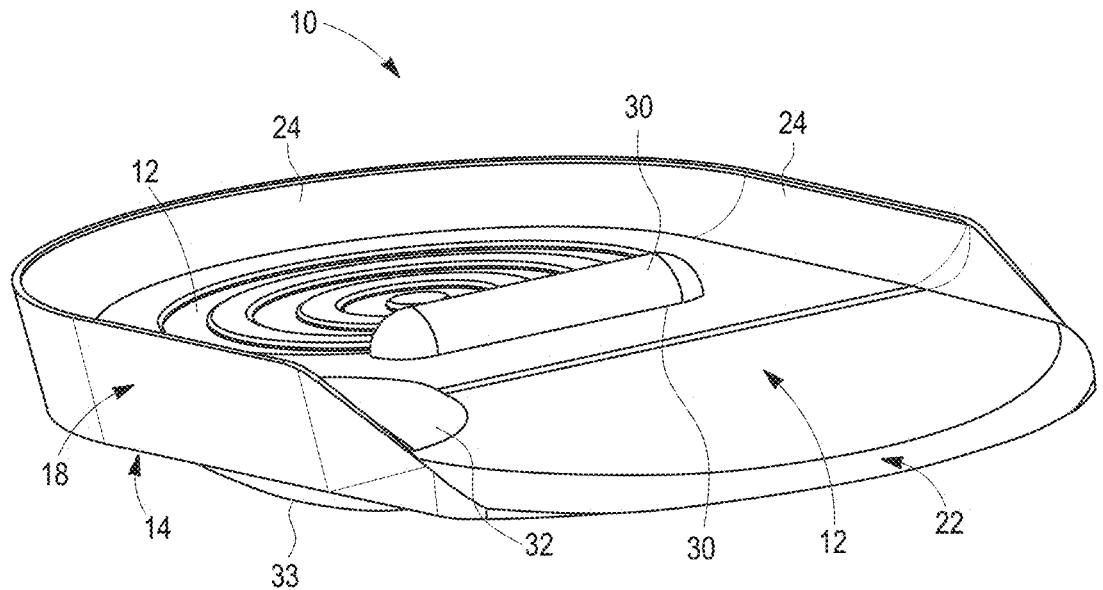
FIG. 4 illustrates another elevational perspective view of the shoe insert device of FIG. 1 according to an embodiment of the present disclosure.
Figure 5:
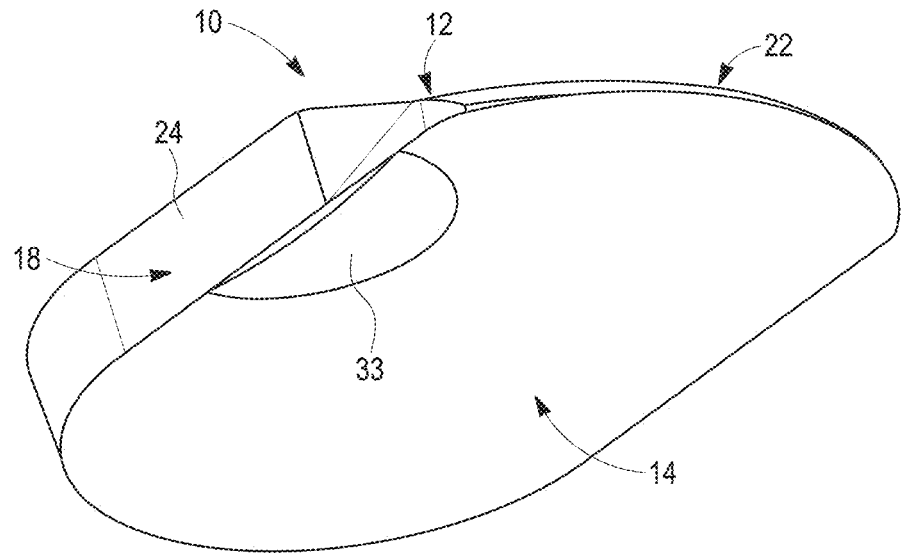
FIG. 5 illustrates a bottom perspective view of the shoe insert device of FIG. 1 according to an embodiment of the present disclosure.
Figure 6:
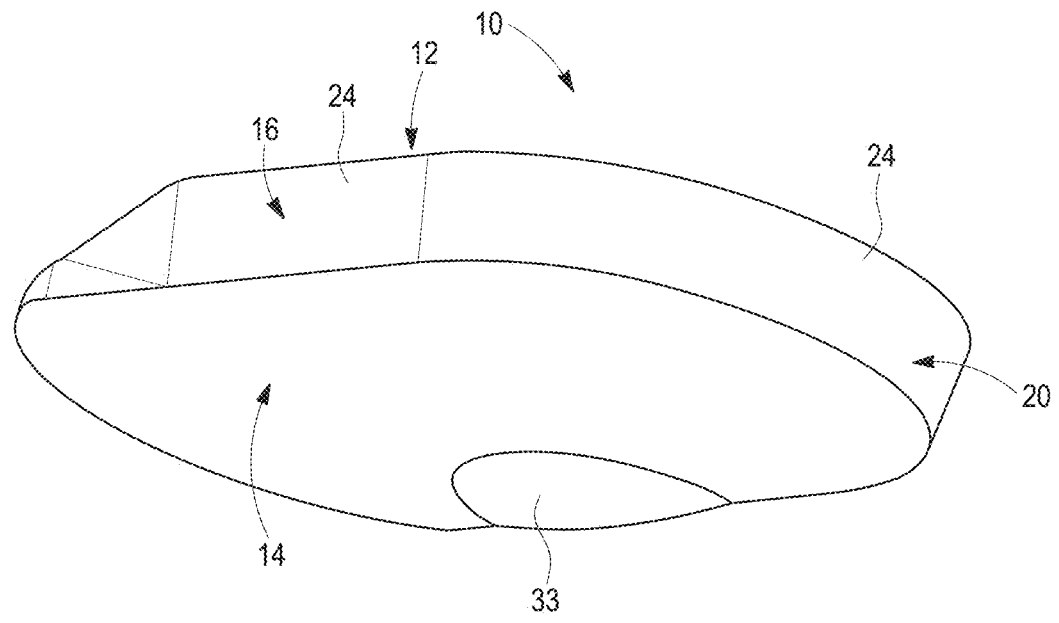
FIG. 6 illustrates another bottom perspective view of the shoe insert device of FIG. 1 according to an embodiment of the present disclosure.
Figure 7:
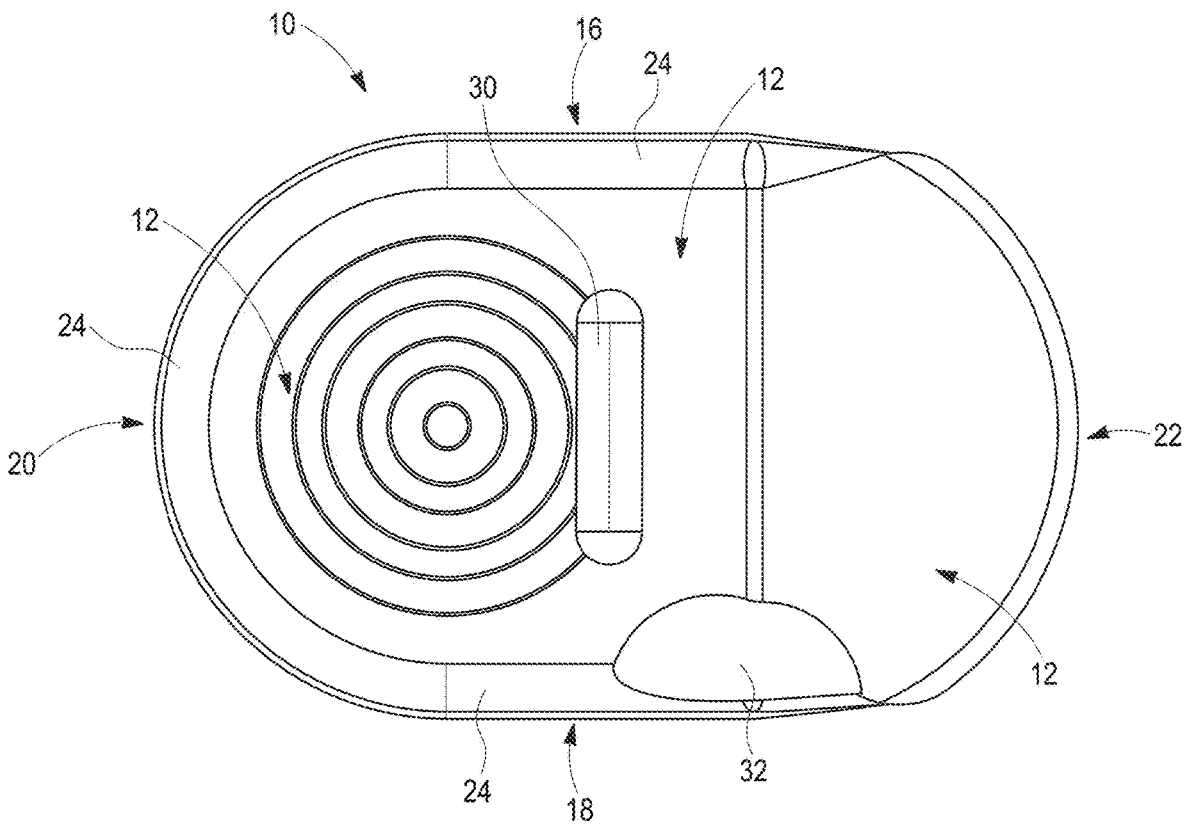
FIG. 7 illustrates a top view of the shoe insert device of FIG. 1 according to an embodiment of the present disclosure.
Figure 8:
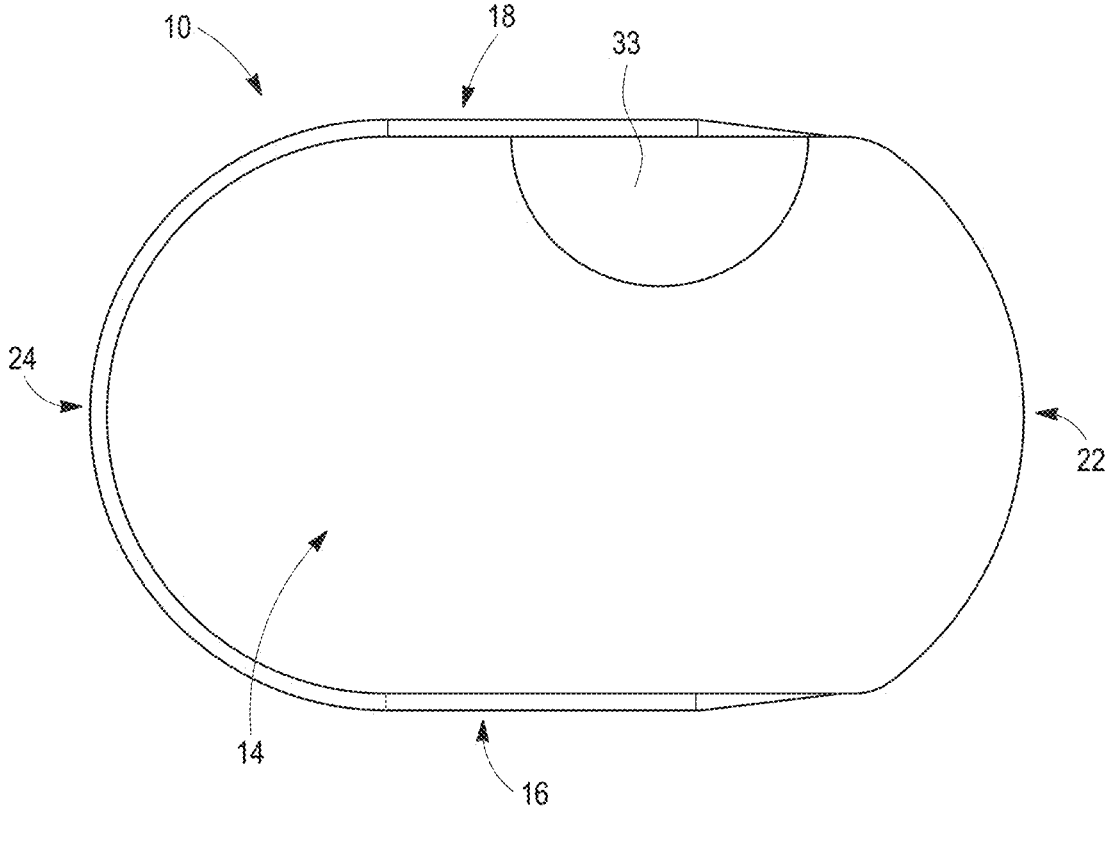
FIG. 8 illustrates a bottom view of the shoe insert device of FIG. 1 according to an embodiment of the present disclosure.
Figure 9:
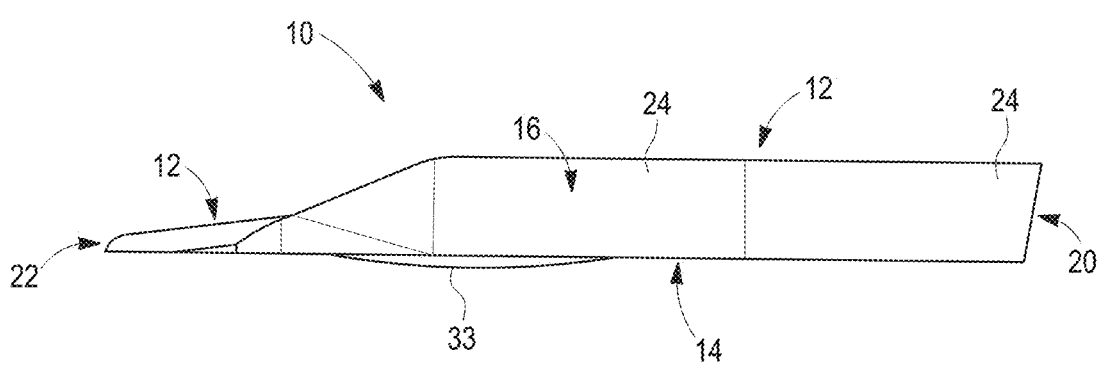
FIG. 9 illustrates a medial view of the shoe insert device of FIG. 1 according to an embodiment of the present disclosure.
Figure 10:
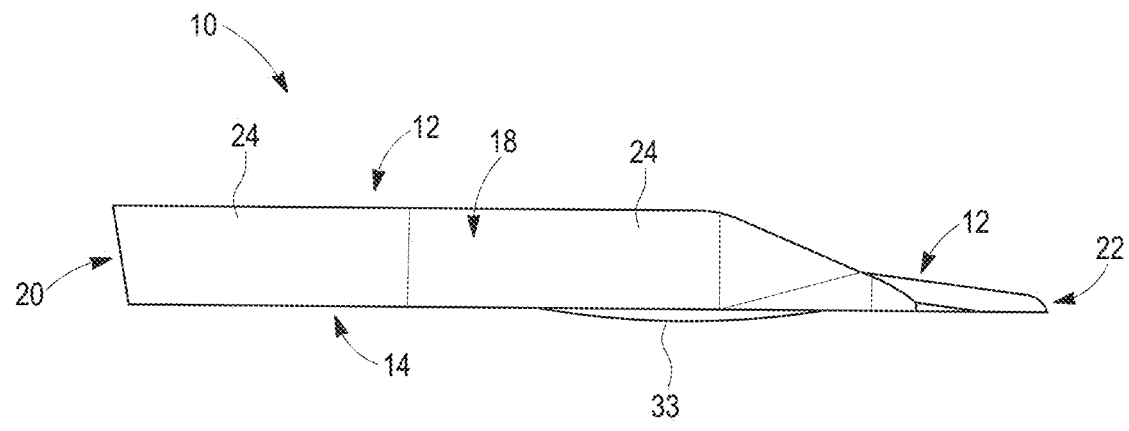
FIG. 10 illustrates a lateral view of the shoe insert device of FIG. 1 according to an embodiment of the present disclosure.
Figure 11:
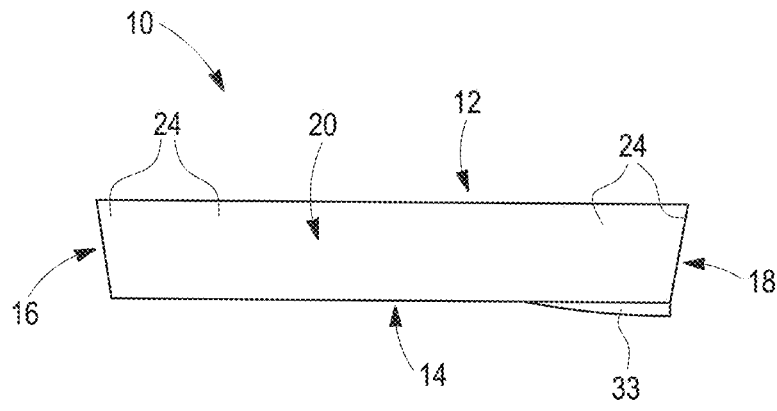
FIG. 11 illustrates a back view of the shoe insert device of FIG. 1 according to an embodiment of the present disclosure.
Figure 12:
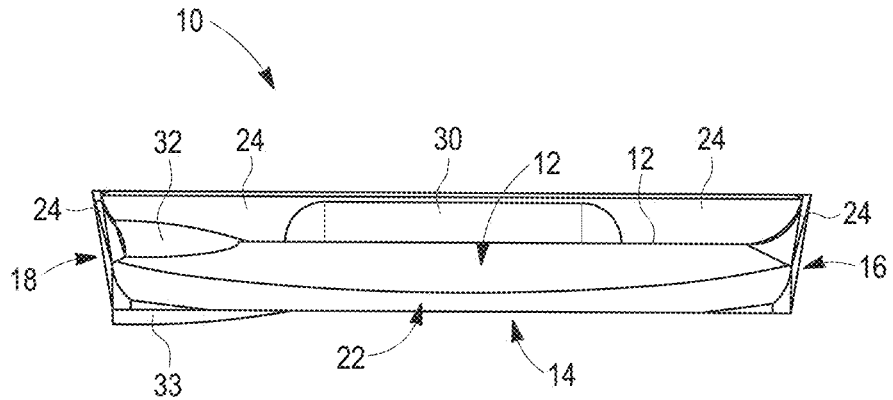
FIG. 12 illustrates a front view of the shoe insert device of FIG. 1 according to an embodiment of the present disclosure.
Figure 13:
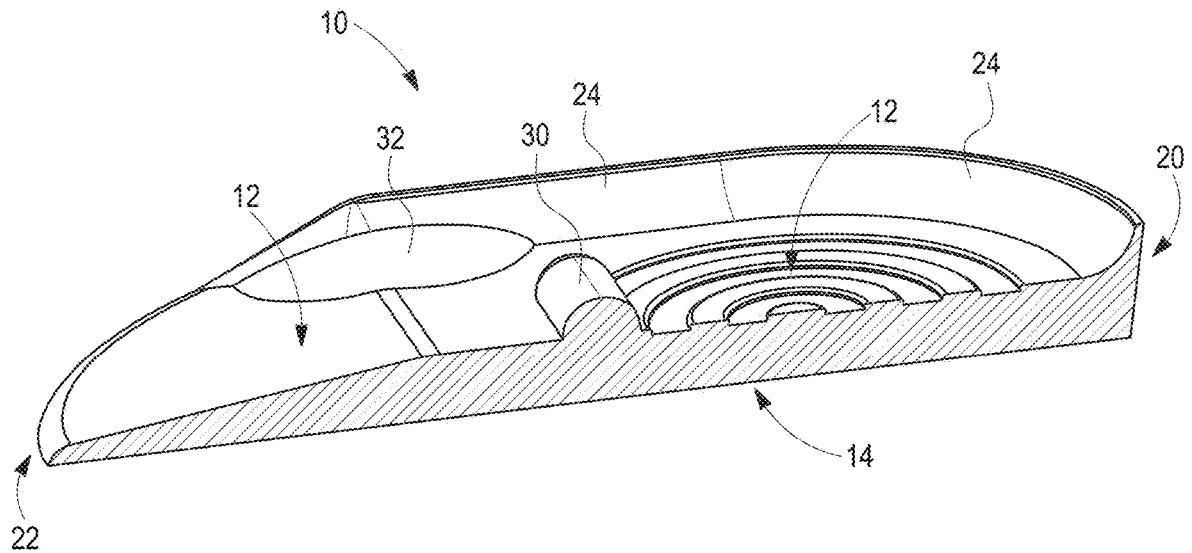
FIG. 13 illustrates an elevational perspective cross-sectional view of the shoe insert device of FIG. 1 according to an embodiment of the present disclosure.

Aspects of the present disclosure and certain examples, features, advantages, and details thereof, are explained more fully below with reference to the non-limiting examples illustrated in the accompanying drawings. Descriptions of well-known components, aspects, materials, chemicals, fabrication mechanisms, processing techniques, uses, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "terms "substantially", "approximately", "about", "relatively," or other such similar terms is not limited to the precise value specified, and is used to describe and account for small fluctuations, such as due to variations in processing, from a reference or parameter. Such small fluctuations include a zero fluctuation from the reference or parameter as well. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

The terms "affix," "connect" "contact," "coupled" and/or the like are broadly defined herein to encompass a variety of divergent arrangements and assembly techniques. These arrangements and techniques include, but are not limited to (1) the direct joining of one component and another component with no intervening components therebetween (i.e., the components are in direct physical contact); and (2) the joining of one component and another component with one or more components therebetween, provided that the one component being "affixed to," "connected to," "contacting" or 'coupled to" the other component is somehow in operative communication with the other component (notwithstanding the presence of one or more additional components therebetween). It is to be understood that some components that are in direct physical contact with one another may or may not be in fluid contact with one another. Moreover, two components that are fluidly/fluidically connected, fluidly/fluidically coupled or in fluid/fluidic communication may or may not be in direct physical contact, and one or more other components may be positioned therebetween.

As shown in FIGS. 1-13, the present disclosure provides a shoe insert device, such as a hindfoot shoe inserts 10 (and methods utilizing such an insert) that absorbs shock and that redistributes forces within a user's foot and/or knee during use. The hindfoot shoe insert 10 includes projections 30, 32 that are configured to reduce the tension at the attachment of the plantar fascia and the medial tubercle of the calcaneus bone of a user's foot, as shown in FIGS. 1-13. The hindfoot shoe insert 10 is also configured to decrease the loading in the medial part of the knee of a user. The hindfoot shoe insert 10 is also configured to reduce the amount of stress in the heel fat pad of a user. The hindfoot shoe insert 10 may also reduce the stress on lateral ankle ligaments, lower back, pelvis/pelvic posture, and/or the Achilles tendon of a user.

With reference to FIGS. 1-13, the shoe insert device 10 is a hindfoot shoe in that is configured to be positioned within a shoe, and extend beneath a hindfoot insert 10 of a sole of a foot of a user within the shoe with a top side 12 of the hindfoot insert 10 facing the sole (i.e., bottom of the user foot). The hindfoot insert 10 may thereby be manually positioned within a user's shoe on the insole, floor, or interior base portion of the shoe. The hindfoot insert 10 comprises a back or proximal end or side 20, a front or distal end or side 22 (that may oppose the proximal end 20), a medial or inner side or end 14 extending between the proximal and distal ends 20, 22, and a lateral or outer side or end 18 (that may oppose the medial side 14) extending between the proximal and distal ends 20, 22. As also shown in FIGS. 1-13, the shoe insert device 10 includes a top or upper side or end 12 and a bottom or lower side or end that opposes the top side 12.

It is noted that the insert device 10 shown in FIGS. 1-13 is configured as a "right" shoe insert device 10 configured for a right shoe and foot. Further, it is contemplated and hereby disclosed that the insert device 10 may alternatively be configured as a "left" shoe insert device 10 for a left shoe and foot by mirroring (or flipping) the insert 10 along the medial direction, as one of ordinary skill in the art would be aware. As such, the anatomical directional terms are used herein for consistency and reference to the features of the insert 10.

The hindfoot shoe insert 10 also includes a fascia projection 30 that extends upwardly from the top surface 12 and is positioned medially between the medial and lateral sides 16, 18, as shown in FIGS. 1-13. The fascia projection 30 is spaced distally from the proximal end 20. The fascia projection 30 may be distally positioned such that it applies upward pressure or force to the portion of a user's planter facia that connects to the medial tubercle of the calcaneus bone of the user's foot (or proximate thereto). For example, fascia projection 30 may be distally positioned such that it is distal to the center of the heel fat pad of the user's foot, such as at least about 1½ cm distal of the center of the heel fat pad of the user's foot. In some embodiments, the fascia projection 30 is spaced distally from the proximal end 20 within the range of about 1 inch to about 4 inches, or within the range of about 1½ inch to about 3 inches. In some embodiments, the fascia projection 30 is spaced distally from the proximal end 20 within the range of about 1½ inches to about 2¾ inches. It is noted, however, that the location of the fascia projection 30 may depend upon the size of a potential user's foot so that it applies upward pressure or force to user's planter facia, such as the portion thereof that connects to the medial tubercle of the calcaneus bone of the user's foot (or proximate thereto). The fascia projection 30 may be resilient at least along the thickness direction.

As also shown in FIGS. 1-13, the hindfoot shoe insert 10 may further include a top or upper lateral projection 32 extending upwardly from the top surface 12 of the hindfoot insert 10 and/or a bottom or lower lateral projection 33 extending downwardly from the bottom surface 12 of the hindfoot insert 10. The upper lateral projection 32 and/or the lower lateral projection 33 may be positioned proximate to the lateral side 18 of the insert 10, and at least partially distal to the fascia projection 30.

The fascia projection 30 and the upper lateral projection 32 and/or the lower lateral projection 32 are configured to reduce the tension at the attachment of the plantar fascia into the medial tubercle of the user's foot, decrease the loading in the medial part of the knee of the user, and reduce the amount of stress in the heel fat pad of the user's foot. For example, the upper lateral projection 32 and/or the lower lateral projection 32 are configured to biomechanically reduce the tension at the insertion point of the plantar fascia into the medial tubercle of the calcaneus of the user's foot. The upper lateral projection 32 and/or the lower lateral projection 32 acts to lock the calcaneocuboid joint, thereby decreasing the strain on the plantar fascia of the user. This the upper lateral projection 32 and/or the lower lateral projection 32 also reduces the stress in the medial compartment of the knee of the user, which is beneficial therapeutically and may prevent overuse and/or the development of osteoarthritis. The fascia projection 30 is configured to apply upward pressure to the insertion point of the plantar fascia of the user (potentially creating a "bow-stringing" effect) that decreases tension and stress around the plantar fascia insertion.

The hindfoot insert 10 may be configured to be resilient (i.e., elastically deformable) at least in a thickness direction extending between the top and bottom sides 12, 14 thereof. For example, the hindfoot insert 10 may be made from one or more resilient materials. In some embodiments, the hindfoot insert 10 may be made from one or more rubber or like material, such as silicone, EPDM, latex, neoprene, or a combination thereof. In some embodiments, the hindfoot insert 10 may be made from one or more plastic or like material, such as polyethylene, polypropylene, nylon, PET, PVC, ABS, a low temperature thermoplastic material or a combination thereof. In some embodiments, the hindfoot insert 10 may be made from one or more foam or like material, such as an EVA foam material, a polyurethane foam material, a silicone foam material, a neoprene foam material, or a combination thereof. In some embodiments, the hindfoot insert 10 may be made from one or more natural or renewable material, such as cork, mushroom leather, animal leather, cotton, natural woven or non-woven fabric, wool, cellulose, or a combination thereof. In some embodiments, the hindfoot insert 10 may be made from one or more gel material, such as a silicone gel, a polyurethane gel, or a combination thereof. The hindfoot insert 10 may be formed of a single material, or a plurality of materials coupled together.

Similarly, the hindfoot insert 10 may be integral or of one-piece construction, or may be formed of a plurality of separate components that are coupled together. In one exemplary embodiment, the hindfoot insert 10 is of one-piece construction, and may be monolithic. In another exemplary embodiment, the hindfoot insert 10 comprises a base or main portion to which a fascia projection or bump 30 and/or a lateral projection or bump 32 are coupled. For example, in some such embodiments, the fascia projection or bump 30 and/or the lateral projection or bump 32 may be modular components that removably couple with the base or main portion. Such an embodiment allows for differing fascia projections 30 and lateral projections bump 32 (e.g., of differing heights, resiliencies, etc.) to be utilized with the base or main portion to suit a particular user.

As shown in FIGS. 1-13, the fascia projection 30 may be extended along the medial-lateral direction such that it defines a length along the medial-lateral direction that is greater than its length along the proximal-distal direction. In some embodiments, the fascia projection 30 defines a length along the medial-lateral direction of at least about 2 cm. In some embodiments, the fascia projection 30 defines a length along the medial-lateral direction within the range of about 2 cm to about 5 cm. In some embodiments, the fascia projection 30 defines a length along the proximal-distal direction of less than about 1½ cm. In some embodiments, the fascia projection 30 defines a length along the proximal-distal direction within the range of about ½ cm to about 1½ cm.

In some embodiments, the fascia projection 30 defines a maximum height from the top surface 12 of the insert 10 adjacent to the fascia projection 30 of at least about ¼ inch. In some embodiments, the fascia projection 30 defines a maximum height from the top surface 12 adjacent to the fascia projection 30 within the range of about ¼ inch to about ¾ inch. However, in some other embodiments, the fascia projection 30 may be of different sizes and/or different shapes.

In some embodiments, the fascia projection 30 is convex along the proximal-distal direction, as shown in FIGS. 1-13. For example, the fascia projection 30 may be arcuately convex along the proximal-distal direction. In the exemplary illustrative embodiment of FIGS. 1-13, the fascia projection 30 includes a cylindrical-shaped portion that extends along the medial-lateral direction.

As shown in FIGS. 1-13, in some embodiments a proximal portion of the lateral projection 32 may be aligned with at least a portion of the fascia projection 30 along the proximal-distal direction. In some other embodiments, however, the lateral projection 32 may be spaced from the fascia projection 30 along the proximal-distal direction.

The lateral projection 32 may be convex along the proximal-distal direction, as shown in FIGS. 1-13. For example, the lateral projection 32 may be arcuately convex along the proximal-distal direction. In some embodiments, the lateral projection 32 is convex along the medial-lateral direction. For example, the lateral projection 32 may include a lateral portion that is positioned further away from the top surface 12 than a medial portion or end thereof, as shown in FIGS. 1-13. In this way, as shown in FIGS. 1-13, the lateral projection 32 may extend downwardly from a lateral side or end thereof to the medial side or end thereof. For example, the lateral projection 32 may extend arcuately downwardly from the lateral side thereof to a medial side thereof. However, in some other embodiments, the lateral projection 32 may be of different sizes and/or different shapes.

In some embodiments, the lateral projection 32 defines a length along the medial-lateral direction of less than about 1½ inches. In some embodiments, the lateral projection 32 defines a length along the medial-lateral direction within the range of about ½ inch to about 1½ inch. In some embodiments, the lateral projection 32 defines a length along the proximal-distal direction of less than about 2½ inches. In some embodiments, the lateral projection 32 defines a length along the proximal-distal direction within the range of about ½ inch to about 2 inches.

In some embodiments, the lateral projection 32 defines a maximum height from the top surface 12 of the of the hindfoot insert 10 adjacent to the lateral projection 32 of at least about ¼ inch. In some embodiments, the lateral projection 32 defines a maximum height from the top surface 12 adjacent to the lateral projection 32 within the range of about ¼ inch to about ¾ inch.

In some embodiments, the upper lateral projection 32 defines a first maximum height from the top surface 12 adjacent to the lateral projection 32, and the fascia projection 30 defines a second maximum height from the top surface 12 adjacent to the fascia projection 30, and wherein the first maximum height is within 25% of the second maximum height. In some embodiments, the first maximum height is less than the second maximum height, as shown in FIGS. 1-13.

In some embodiments, the lateral projection 32 is resilient at least along the thickness direction. In some embodiments, the fascia projection 30 and the lateral projection 32 have substantially the same modulus of resilience at least along the thickness direction. In some embodiments, the fascia projection 30 and the lateral projection 32 are formed of the same material.

As discussed above and shown in FIGS. 1-13, the hindfoot shoe insert 10 may include a bottom or lower lateral projection 33 extending downwardly from the bottom surface 12 of the hindfoot insert 10, such as in addition to (or instead of) the upper lateral projection 32 extending upwardly from the top surface 12 of the hindfoot insert 10.

The bottom lateral projection 33 may be of the same or similar location, shape and/or size (or other configuration) as the upper lateral projection 32 described above. For example, the bottom lateral projection 33 may define a maximum height from the bottom surface 14 of the hindfoot insert 10 that is adjacent to the bottom lateral projection 33 of at least about ¼ inch. In some embodiments, the bottom lateral projection 33 may define a maximum height from the bottom surface 14 adjacent to the bottom lateral projection 33 within the range of about ¼ inch to about ¾ inch.

As shown in FIGS. 1-13, the hindfoot shoe insert 10 may include both the upper lateral projection 32 extending upwardly from the top surface 12 and the bottom lateral projection 33 extending downwardly from the bottom surface 12 of the hindfoot insert 10. In some such embodiments, the bottom lateral projection 33 may extend downwardly from the bottom surface 12 and define a first maximum height, the upper lateral projection 32 may extend upwardly from the top surface 12 and define a second maximum height, and the first maximum height may be within 25% of the second maximum height. In embodiments, the first maximum height and the second maximum height may be the same equal (i.e., the upper lateral projection 32 and the lower lateral projection 33 may be of the same heights, but extend in opposing directions). In some embodiments, the upper lateral projection 32 may have a first modulus of resilience, and the lower lateral projection 33 may have a second modulus of resilience that differ from the first modulus of resilience. In some such embodiments, the first modulus of resilience may be greater than the second modulus of resilience.

As shown in FIG. 1, the hindfoot insert 10 may include a proximal portion 26 that is configured to extend beneath a heal fat pad of a heal of the foot of the user that defines the proximal end 20 of the hindfoot insert 10. As also shown in FIG. 1, the hindfoot insert 10 may further include a distal portion 28 that extends distally from the proximal portion 26 and defines the distal end 22 of the hindfoot insert 10. The proximal portion 26 and the distal portion 28 may cooperatively form the hindfoot insert 10, such as including the top surface 12 and the bottom surface 14 thereof. In some embodiments, as shown in FIGS. 1-13, the thickness of the distal portion 28 may vary at least along the proximal-distal direction. For example, the portion of the top surface 12 formed by the distal portion 28 of the hindfoot insert 10 may thereby extend downward from the proximal portion 26. In some embodiments, the proximal portion of the top surface 12 formed by the proximal portion 26 of the hindfoot insert 10 is substantially planar. In some embodiments, the distal portion of the top surface 12 formed by the distal portion 28 of the hindfoot insert 10 is substantially planar.

As shown in FIGS. 1-13, in some embodiments, the fascia projection 30 may positioned on the proximal portion 26 of the hindfoot insert 10. In some embodiments, at least a portion of the upper lateral projection 32 and/or lower lateral projection 33 is positioned on the distal portion 28 of the hindfoot insert 10. In some embodiments, at least a portion of the lateral projection 32 is positioned on the proximal portion of the hindfoot insert 10.

In some embodiments, the hindfoot insert 10 may include a peripheral rim portion or member 24 that extends upwardly from the top surface 12 and along the medial side 14, the proximal end 20 and the lateral side 18 thereof, as shown in FIGS. 1-13. The peripheral rim portion 24 may extend along only a portion of the medial and lateral sides 14, 18, such as a distal portion thereof. The inner or interior side of the rim portion 24 may extend from the top surface 12, such as arcuately extend therefrom. In some embodiments, the inner or interior side of the rim portion 24 may be arcuately concave as it extends from the top surface 12. The upper lateral projection 32 may extend medially from the rim member 24.

Another exemplary shoe insert device 110 that absorbs shock and that redistributes forces within a user's foot and/or knee during use, as described above, is shown in FIGS. 14 and 15. The insert device 110 of FIGS. 14 and 15 is substantially similar to the shoe insert device 10 described above with respect to FIGS. 1-13, and therefore like reference numerals preceded with "1" are used to indicate like components, aspects, functions, processes or functions, and the description above directed to thereto equally applies, and is not repeated for brevity and clarity purposes.

Figure 14:
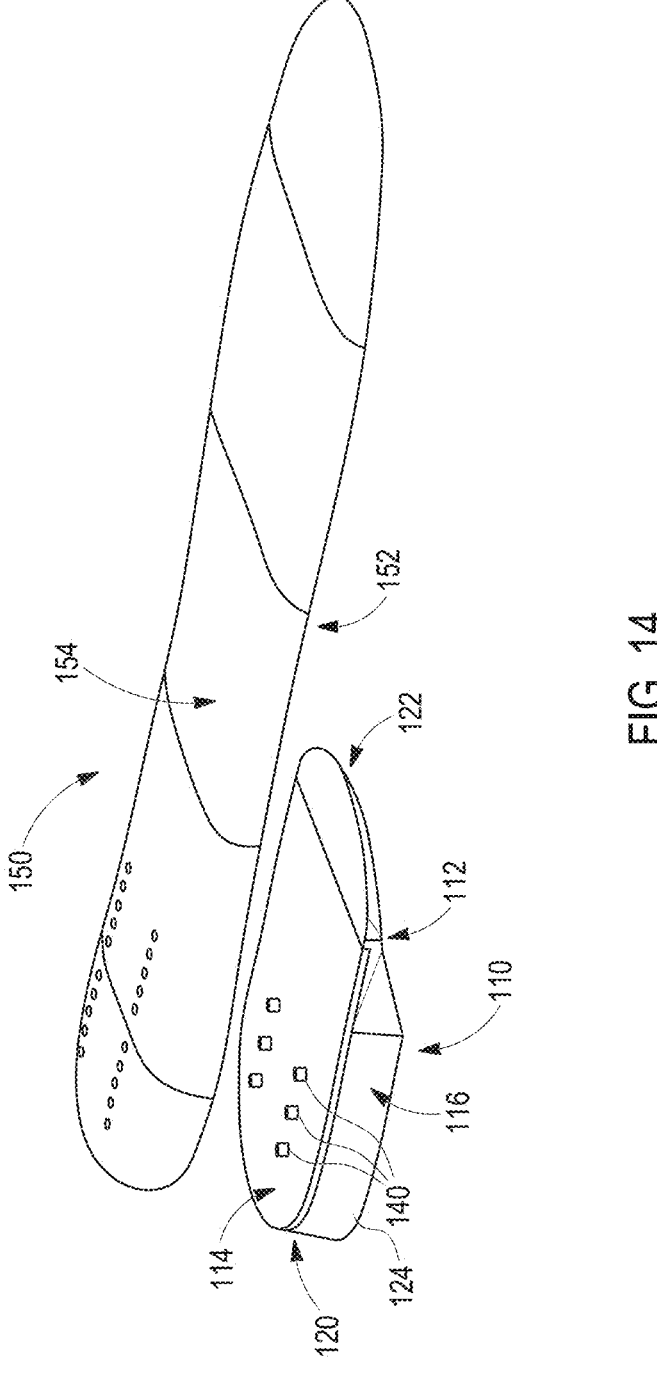
FIG. 14 illustrates a bottom perspective view of another shoe insert device according to an embodiment of the present disclosure.
Figure 15:
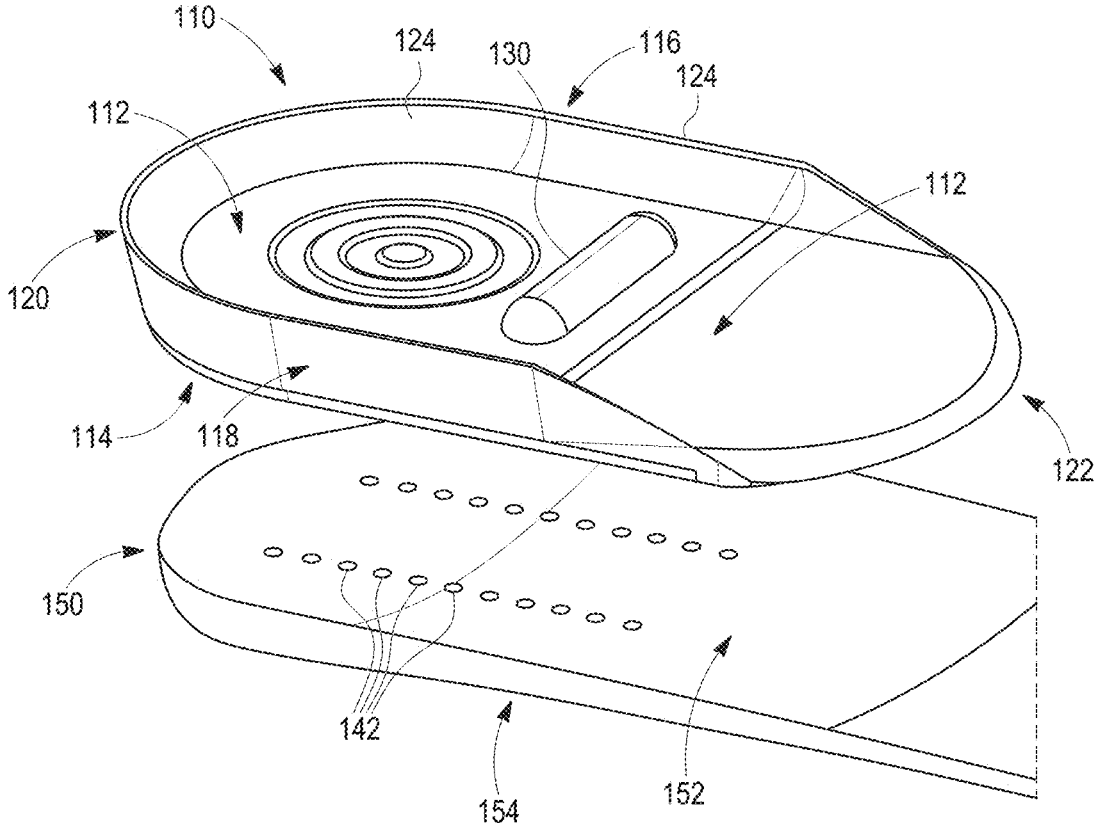
FIG. 15 illustrates an enlarged elevational perspective view of the shoe insert device of FIG. 14 according to an embodiment of the present disclosure.

As shown in FIGS. 14 and 15, the shoe insert device 110 differs from the shoe insert device 10 in that the shoe insert device 10 is configured to couple to an insole or base portion 150. As shown in FIGS. 14 and 15, the shoe insert device 110 includes a plurality of engagement projections, pegs, members 140 or the like that extend away from the bottom side 114. The base portion 150 includes a top side 152 and a bottom side 154, as shown in FIGS. 14 and 15. A proximal portion of the top side 152 of the base portion 150 includes a plurality of engagement cavities 142 that are configured to engage with the plurality of engagement pegs 142 of the shoe insert device 110, as shown in FIG. 15. The base portion 150 may be configured such that the shoe insert device 110 can couple to the proximal portion of the portion 150 in a variety of differing positions.

Another exemplary shoe insert device 210 that absorbs shock and that redistributes forces within a user's foot and/or knee during use, as described above, is shown in FIG. 16. The insert device 210 of FIG. 16 is substantially similar to the insert device 110 and base portion 150 described above with respect to FIGS. 14 and 15, and therefore like reference numerals preceded with "2" are used to indicate like components, aspects, functions, processes or functions, and the description above directed to thereto equally applies, and is not repeated for brevity and clarity purposes.

Figure 16:
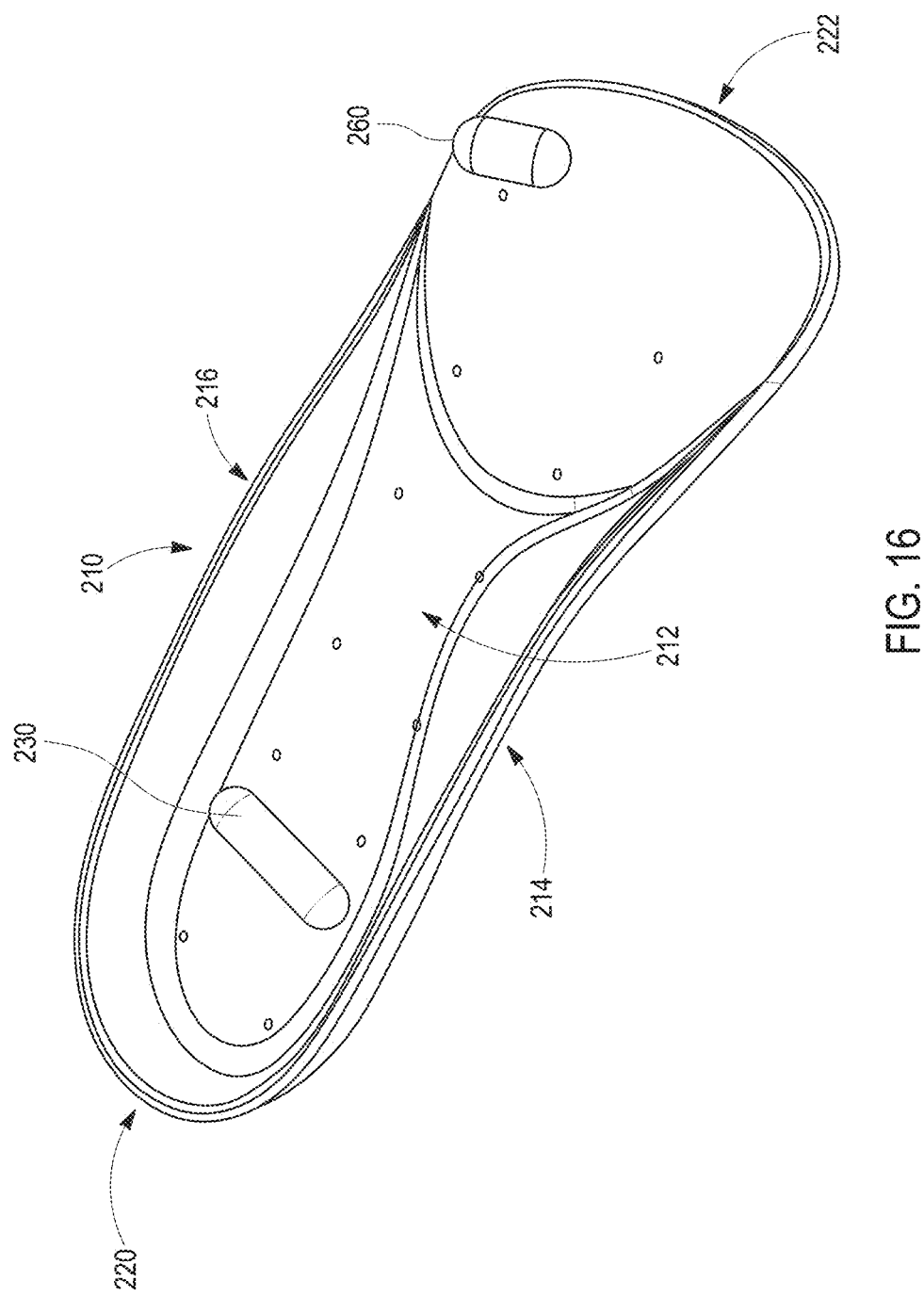
FIG. 16 illustrates an elevational perspective view of another shoe insert device according to an embodiment of the present disclosure.

As shown in FIG. 16, in some embodiments, the shoe insert device 210 differs from the device 110 and the base portion 150 of FIGS. 14 and 15 in that the hindfoot, midfoot and forefoot portions are a single construct or fixedly coupled together. As also shown in FIG. 16, in some embodiments, the shoe insert device 210 differs from the base portion 150 in that the forefoot portion includes a forefoot projection 260 extending upwardly from a top surface 212 thereof. The forefoot projection 260 may be positioned proximate to a lateral side 216 of the device 210 on the distal end of the forefoot portion. The forefoot projection 260 may thereby be configured to be positioned below a distal, middle and/or proximal phalange of the fourth and/or fifth toes of the foot of the user.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples without departing from their scope. While dimensions and types of materials may be described herein, they are intended to define parameters of some of the various examples, and they are by no means limiting to all examples and are merely exemplary. Many other examples will be apparent to those of skill in the art upon reviewing the above description. The scope of the various examples should, therefore, be determined with reference to the claims included herein, along with the full scope of equivalents to which such claims are entitled.

As used herein, the terms "including" and "in which" are used as the plain-English equivalents of the respective terms "comprising" and "wherein." Moreover, as used herein, the terms "first," "second," and "third," etc. are used merely as reference labels, and are not intended to impose numerical, structural, or other requirements. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the claims included herein are not written in means-plus-function format and are not intended to be interpreted based on 35 U. S.C. § 112, sixth paragraph, unless and until such claim limitations expressly use the phrase "means for" followed by a statement of function cavity of further structure. It is to be understood that not necessarily all such objects or advantages described above may be achieved in accordance with any particular example. Thus, for example, those skilled in the art will recognize that the systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions, or equivalent arrangements not heretofore described, but which are commensurate with the spirit and scope of the disclosure. Additionally, while various examples have been described, it is to be understood that aspects of the disclosure may include only one example or some of the described examples. Also, while some disclosures are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A shoe insert device, comprising:
a hindfoot insert portion comprising a proximal end, a distal end, a medial side extending between the proximal and distal ends, a lateral side extending between the proximal and distal ends, a top side and a bottom side,
wherein the hindfoot insert portion is configured to be positioned within a shoe and extend beneath a hindfoot portion of a sole of a foot of a user within the shoe with the top side of the hindfoot insert portion facing the sole,
wherein the hindfoot insert portion is resilient at least in a thickness direction extending between the top and bottom sides,
wherein the hindfoot insert portion comprises:

a fascia projection extending upwardly from the top surface positioned medially between the medial and lateral sides and being spaced distally from the proximal end; and a lateral projection extending upwardly from the top surface positioned proximate to the lateral side and distal to the fascia projection.

2. The shoe insert device according claim 1, wherein the fascia projection is extended along a medial-lateral direction such that it defines a length along the medial-lateral direction that is greater than its length along a proximal-distal direction.

3. The shoe insert device according to claim 2, wherein the fascia projection defines a length along the medial-lateral direction within the range of about 2 cm to about 5 cm.

4. The shoe insert device according to claim 1, wherein the hindfoot insert portion includes a proximal portion that is configured to extend beneath a heal fat pad of a heal of the foot of the user that defines the proximal end and a proximal portion of the top surface, and a distal portion that extends distally from the proximal portion and defines the distal end and a distal portion of the top surface, and wherein the a thickness of the distal portion varies such that the distal portion of the top surface extends downward from the proximal portion of the top surface.

5. The shoe insert device according to claim 4, wherein the fascia projection is positioned on the proximal portion of the hindfoot insert portion.

6. The shoe insert device according to claim 1, wherein the fascia projection defines a length along the proximal-distal direction within the range of about ½ cm to about 1½ cm.

7. The shoe insert device according to claim 1, wherein the fascia projection is spaced distally from the proximal end within the range of about 1 inch to about 3 inches.

8. The shoe insert device according to claim 1, wherein the fascia projection is resilient at least along the thickness direction.

9. The shoe insert device according to claim 1, wherein the fascia projection is convex along the proximal-distal direction.

10. The shoe insert device according to claim 1, wherein the fascia projection includes a cylindrical-shaped portion that extends along the medial-lateral direction.

11. The shoe insert device according to claim 1, wherein the lateral projection includes a lateral portion that is positioned further away from the top surface than a medial portion thereof.

12. The shoe insert device according to claim 1, wherein the lateral projection defines a length along the medial-lateral direction within the range of about ½ inch to about 1½ inch, and defines a length along the proximal-distal direction within the range of about ½ inch to about 2 inches.

13. The shoe insert device according claim 1, wherein the lateral projection defines a maximum height from a portion of the top surface that is adjacent to the lateral projection within the range of about ¼ inch to about ¾ inch.

14. The shoe insert device according to claim 1, wherein the hindfoot insert portion further comprises a peripheral rim member that extends upwardly from the top surface and along the medial side, proximal end and lateral side, and wherein the lateral projection extends medially from the peripheral rim member.

15. The shoe insert device according to claim 1, wherein the bottom surface is substantially planar.

16. The shoe insert device according to claim 1, wherein the device consists of the hindfoot insert portion.

17. A shoe insert device, comprising:

a hindfoot insert portion comprising a proximal end, a distal end, a medial side extending between the proximal and distal ends, a lateral side extending between the proximal and distal ends, a top side and a bottom side, wherein the hindfoot insert portion is configured to be positioned within a shoe and extend beneath a hindfoot portion of a sole of a foot of a user within the shoe with the top side of the hindfoot insert portion facing the sole, wherein the hindfoot insert portion is resilient at least in a thickness direction extending between the top and bottom sides, wherein the hindfoot insert portion comprises:

a fascia projection extending upwardly from the top surface positioned medially between the medial and lateral sides and being spaced distally from the proximal end; and a lateral projection extending at least one of upwardly from the top surface and downwardly from the bottom surface positioned proximate to the lateral side and distal to the fascia projection wherein the lateral projection extends medially from the rim member, wherein the hindfoot insert portion further comprises a peripheral rim member that extends upwardly from the top surface and along the medial side, proximal end and lateral side, and wherein the lateral projection extends medially from the rim member.

18. The shoe insert device according to claim 17, wherein the lateral projection extends upwardly from the top surface.

19. A method of configuring a shoe, comprising:

providing hindfoot shoe insert device comprising a proximal end, a distal end, a medial side extending between the proximal and distal ends, a lateral side extending between the proximal and distal ends, a top side and a bottom side, wherein the hindfoot shoe insert device is configured to be positioned within a shoe and extend beneath at least a hindfoot portion of a sole of a foot of a user within the shoe with the top side of the hindfoot shoe insert device facing the sole, wherein the hindfoot shoe insert device is resilient at least in a thickness direction extending between the top and bottom sides, and wherein the hindfoot shoe insert device comprises a hindfoot portion comprising:

a fascia projection extending upwardly from the top surface positioned medially between the medial and lateral sides and being spaced distally from the proximal end; and a lateral projection extending of upwardly from the top surface positioned proximate to the lateral side and distal to the fascia projection.

20. The method according to claim 19, wherein the hindfoot insert portion of the hindfoot shoe insert device further comprises a peripheral rim member that extends upwardly from the top surface and along the medial side, proximal end and lateral side wherein the lateral projection extends medially from the rim member.

21. A method of adjusting a shoe's foot support profile, comprising:

positioning a hindfoot shoe insert device within a hindfoot area of a shoe such that the hindfoot shoe insert device is positioned beneath at least a hindfoot portion of a sole of a foot of a user within the shoe with a top side of the hindfoot shoe insert device facing the sole, wherein the hindfoot shoe insert device comprises a proximal end, a distal end, a medial side extending between the proximal and distal ends, a lateral side extending between the proximal and distal ends, a bottom side and the top side, wherein the hindfoot shoe insert device is resilient at least in a thickness direction extending between the top and bottom sides, and wherein the hindfoot shoe insert device comprises a hindfoot portion comprising:

a fascia projection extending upwardly from the top surface positioned medially between the medial and lateral sides and being spaced distally from the proximal end; and a lateral projection extending of upwardly from the top surface positioned proximate to the lateral side and distal to the fascia projection.

22. The method according to claim 21, wherein the hindfoot insert portion of the hindfoot shoe insert device further comprises a peripheral rim member that extends upwardly from the top surface and along the medial side, proximal end and lateral side wherein the lateral projection extends medially from the rim member.

* * * * *